United States Patent [19]

Drewlow

[11] Patent Number: Plant 6,298

[45] Date of Patent: Sep. 20, 1988

[54] IMPATIENS PLANT NAMED AURORA

[75] Inventor: Lyndon W. Drewlow, Ashtabula, Ohio

[73] Assignee: Mikkelsens, Inc., Ashtabula, Ohio

[21] Appl. No.: 916,561

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An impatiens plant named Aurora, having rose pink flower color with magenta eye, variegated foliage, early flowering, two flowers per leaf axil, floriferous habit; vigorous, compact and self-branching growth habit, ease of propagation, and having the ability to flower under low light conditions and 70° F. temperature without dropping an excessive amount of leaves.

1 Drawing Sheet

The present invention relates to a new and distinctive cultivar of impatiens plant, botanically known as Impatiens, and referred to by the cultivar name Aurora. Aurora was developed by me through controlled breeding by crossing Mikkelsen Seedling No. 83-726-7 (seed parent) with Mikkelsen Seedling No. 83-730-1 (pollen parent). Asexual reproduction of the progeny of the stated cross by terminal or stem cuttings performed in Astabula, Ohio has shown that unique features of this new impatiens are stabilized and are reproduced true to type in successive propagations.

The following characteristics in combination distinguish the new impatiens from both its parent varieties and other cultivated impatiens of this type known and used in the floriculture industry. In certain instances the characteristics are compared with similar characteristics of other cultivars. Of the cultivars referred to, Dawn is disclosed in U.S. Plant Pat. No. 5,775; Gemini is disclosed in U.S. Plant Pat. No. 5,132; Columbia is disclosed in U.S. Plant Pat. No. 5,126; and Equinox, Zenith and Nova are disclosed in pending applications.

1. Aurora is a smaller plant than Equinox and Zenith, more mounded and smaller than Columbia, similar in size to Nova, and larger than Dawn.

2. Aurora has a more rose pink flower color than Equinox (a light pink), Dawn (a dark pink), and Columbia (a medium pink), but not as deep a rose as Gemini.

3. Aurora has a distinct magenta eye that extends to the lower areas of the petals except for the upper petal, which is similar to Equinox. Columbia has only a small area of magenta at the center of the flower, and Dawn has a whitish area at the center of the flower.

4. The flowers of Aurora are larger in diameter than Dawn, similar to Equinox and Columbia, but not as large as the flowers of Zenith. Petals overlap resulting in an almost circular flower.

5. Leaf color is similar to Nova as is the variegation pattern. However, it does not have small hairs on the upper leaf surface like Nova. It also has a lighter dark green (deep red pigment) leaves and heavier variegation than Equinox. Both Dawn and Columbia have bright green leaves, with cream variegation.

6. Aurora has a leaf that is similar in shape and size to Equinox, Columbia and Zenith, while Dawn has a smaller leaf.

7. Aurora has demonstrated the ability to remain in bloom under high temperatures and sunlight without burn to the foliage.

8. Aurora is an early flowering cultivar, being similar to Equinox, Dawn and Columbia in flowering time.

9. Leaf margin of Aurora is entire with fine cilia similar to Equinox, while Columbia and Dawn have finely serrated leaves with fine cilia.

10. Aurora has two flowers per leaf axil which is similar to Nova, while Equinox only rarely has two flowers per leaf axil and Dawn and Columbia only have one flower per leaf axis.

11. Aurora is a compact, highly self-branched and floriferous cultivar with flowers carried above the foliage, thereby making it suited for 4-inch, 6-inch and hanging basket use.

The accompanying colored photograph is in perspective showing the overall appearance of Aurora, and showing the colors as true as it is reasonably possible to obtain in a colored reproduction of this type.

The following is a detailed description of Aurora based on plants produced under commercial practices in Ashtabula, Ohio under both greenhouse and outdoor conditions. Photographs were taken on greenhouse grown plants in early June. Color references are made to the Royal Horticultural Society Colour Chart except where general terms of ordinary dictionary significance are used.

Parentage: A controlled cross between Mikkelsen Seedling No. 83-726-7 with Mikkelsen Seedling No. 83-730-1.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant Description:

(A) *Form.*—Compact, symmetrically mounded, self-branching, red stemmed, vigorous growing herb.

(B) *Habit of growth.*—Vigorous, self-branching, compact, mounded, continuous flowering.

(C) *Foliage description.*—Dark green leaves with a tint of purple on the mature leaves, with cream variegation in the center of the leaf extending about two-thirds of the way up the leaf. (1) Size: 10 to 12 cm long by 2.5 to 3.5 cm wide. (2) Shape: Lanceolate with acuminate apex and acute base. (3) Texture: Upper side slightly rugose and lower side glabrous. (4) Margin: Entire with fine cilia. (5) Color: Young foliage top side 146A base, variegation 20A near 183B in center. Under side: variegation 171C. Mature foliage top side 147A base, variegation 20A near 183B in center. Under side: 171C. (6) Venation: Pinnate, veins are red in color.

Flowering description:

(A) *Flowering habits.*—Flowers continuously from leaf whorl in progressively orderly manner, taking 5 to 7 days from bud to bloom; flowers last 2–3 weeks. There are usually two flower buds per leaf axil and first flowers for all leaf axils in a whorl open before the secondary ones start to open.

(B) *Natural flowering season.*—Indeterminant and continuous. Quantity of flowering increases with increasing levels of light.

(C) *Flower buds.*—Ellipsoidal, flowers perfect, red spur 3.5 cm long with throat behind ovary and originating from a major sepal.

*Flowers borne.*—On individual pedicels between 4.5 and 5.0 cm long from a whorl of 5 leaves, flowering progressively around the whorl as leaves and buds develop with first flowers from a leaf axil just above the leaf canopy and the second flower just inside the canopy. Second flower from axil does not open until all first flowers are open in a whorl.

(E) *Quantity of flowers.*—Very floriferous due to multiple flowering from a leaf axil.

(F) *Petals.*—(1) Shape: Heart shaped with upper petal slightly larger. (2) Color: Top side in summer when opening, 55B, with center eye 57A; fades to 55C; under side is 55B with stripes of 57A. (3) Number of petals: Five (5) in number. (4) Size of complete flower: 4 to 5 cm.

(G) *Reproductive organs.*—(1) Stamens: Five (5) in number. (a) Anther shape: Hooded, color cream with purple tinge. (b) Pollen color: Cream. (2) Pistels (a) Stigma: Five (5) in number, segmented column shaped, color purplish. (b) Style color: Purplish. (c) Ovaries: Five (5) in number, size 5 mm until fertilized, purplish in color.

Disease resistance: No significant disease or insect problems noted to date.

SUMMARY OF IMPORTANT CHARACTERISTICS OF NEW CULTIVAR

1. Distinct magenta dye that extends to the lower petals.
2. Two flowers are formed at most leaf axils.
3. Rose pink flower with distinct magenta eye contrasted with dark green foliage with cream variegation produces a very pleasing contrast.
4. Aurora has the ability to flower under low light condition and 70° F. without dropping an excessive amount of leaves for four weeks.
5. Good cutting production for propagation purposes.

I claim:

1. A new and distinct impatiens plant named Aurora, as described and illustrated, and particularly characterized by its rose pink flower color with magenta eye, variegated foliage, early flowering, two flowers per leaf axil, floriferous habit; vigorous, compact and self-branching growth habit, ease of propagation, and by its ability to flower under low light conditions and 70° F. temperature without dropping an excessive amount of leaves.

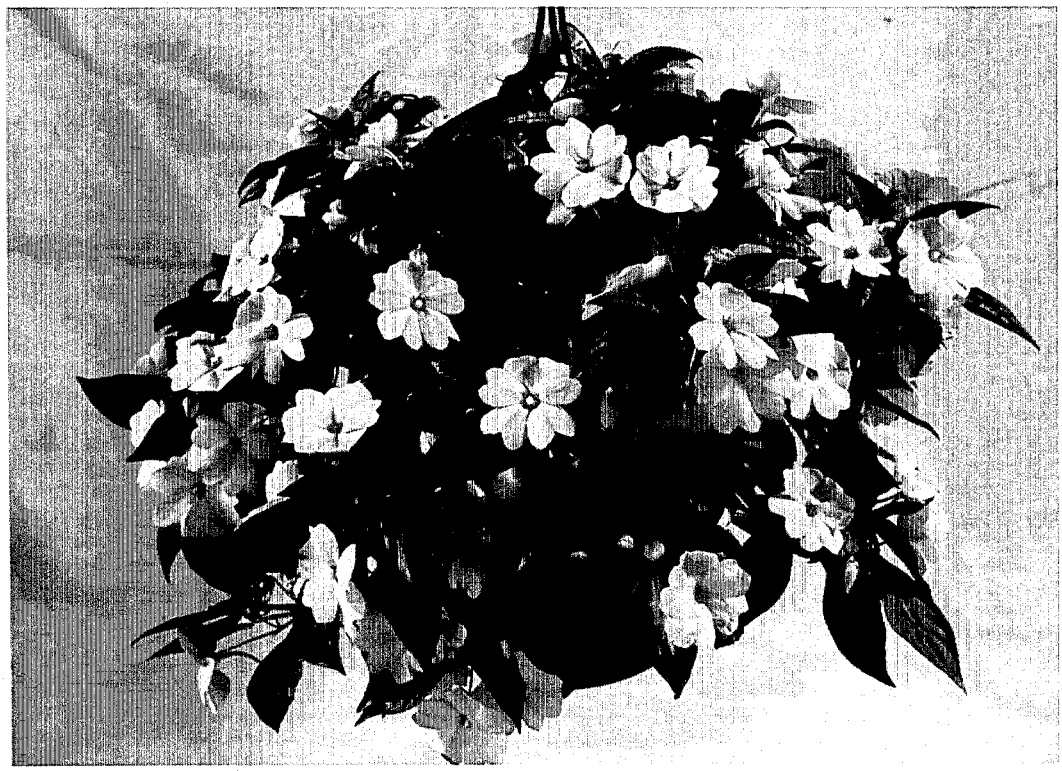

* * * * *